United States Patent [19]

Yamashita et al.

[11] 4,083,960
[45] Apr. 11, 1978

[54] METHOD OF PREVENTING DIARRHEA FOR YOUNG PIG AND CALF

[75] Inventors: Kiyoshi Yamashita, Kawagoe; Hidehiko Kudo, Chiba, both of Tokyo, Japan

[73] Assignees: Kaken Chemical Co., Ltd.; Godoshusei Company, Limited, both of Japan

[21] Appl. No.: 763,242

[22] Filed: Jan. 27, 1977

[30] Foreign Application Priority Data

Feb. 16, 1976 Japan .................................. 51-14831

[51] Int. Cl.$^2$ ............................................ A61K 37/48
[52] U.S. Cl. ..................................................... 424/94
[58] Field of Search ......................................... 424/94

[56] References Cited

PUBLICATIONS

Kutas et al., — Chem. Abst., vol. 78 (1973) p. 145,926b.
Weijers et al., — Chem. Abst., vol. 58 (1963) p. 3765c.
Weijers et al., — Chem. Abst., vol. 63 (1965) p. 16921f.

*Primary Examiner*—Sam Rosen
*Attorney, Agent, or Firm*—Oblon, Fisher, Spivak, McClelland & Maier

[57] ABSTRACT

Diarrhea of young pig and calf in the sucking or weaning period is prevented by an oral dosage of $\beta$-galactosidase.

7 Claims, No Drawings

METHOD OF PREVENTING DIARRHEA FOR YOUNG PIG AND CALF

BACKGROUND OF THE INVENTION

1. Field of the Invention

The present invention relates to a method of preventing diarrhea for young pig and calf.

2. Description of the Prior Art

Young pigs easily suffer diarrhea. It has been reported that 60 to 70% of young pigs suffer diarrhea in the sucking or weaning period. Without any therapeutics, these young pigs cause remarkable weight losses and someones may die because of the diarrhea or the secondary infection caused by the diarrhea. Even though they can survive, the growth is not enough and the commercial value is lowered. The diarrhea may be caused by various reasons such as infections to virus, bacteria, parasite, etc., disturbance of nitrition, intoxication etc. Various therapeutic treatments such as administrations of antibiotics, sulfadiazines etc. have been tried. However, satisfactory results could not be attained because of drug resistant bacteria or other complicated causes.

One of serious diseases of calf is diarrhea. Recently fat growth method for calf has been carried out in a large scale, and the trouble of diarrhea has been close-up.

The diarrhea may be also caused by various reasons such as those of young pigs.

It has been reported that 30 to 50% of calves suffer from diarrhea in the sucking or weaning period, and the secondary infection for the other diseases is caused by the diarrhea and death occurs in about 50% of the calves.

Various therapeutic treatments such as administrations of antibiotics, sulfadiazines, vaccines, etc. have been tried. However, satisfactory results could not be attained both in young pig and calf. Most of the diarrhea are infectious and the damage caused by the diarrhea is serious from the commercial viewpoint.

SUMMARY OF THE INVENTION

It is an object of the present invention to provide a method of preventing diarrhea for young pig and calf in the sucking or weaning period for preventing a decrease of productivity and promoting growth of young pig and calf.

The object of the present invention has been attained by an oral dosage of β-galactosidase.

DESCRIPTION OF THE PREFERRED EMBODIMENTS

The prevention of diarrhea means the prevention before and after suffering from the diarrhea in sucking and weaning period.

β-galactosidase is 3,2,1, 23β-D-galactoside-galactohydrolase which is capable of not only decomposing and synthesizing lactose, but also hydrolyzing alkyl- or aryl-β-D-galactosides and some of the enzyme can transfer galactose residual group to the other saccharides, alcohols and phenols. The β-galactoside slightly affects to the β-arabinoside or β-glucoside bond. Accordingly it differs from the β-glucosidase.

The β-galactosidase can be produced by culturing *Kluyveromyces lactis*, *K. fragilis*, *Torulopsis cremoris*, *T. utilis*, *Escherichia coli*, *Lactobacillus bulgaricus*, *Aspergillus oryzae*, *A. flavus*, and *A. niger*.

The β-galactosidase can be obtained from various origins and can be isolated from the culture medium.

For example, the β-galactosidase can be isolated from the culture medium of *Kluyveromyces lactis* by filtering yeast mycelia from the culture medium and extracting the enzyme from the mycelia with toluene, precipitating the enzyme by adding acetone or isopropyl alcohol to the extract, dissolving the crude enzyme in cold water, filtering it, dissolving glucose or maltose in the aqueous solution of the enzyme and drying the mixture by a freeze-drying method to obtain the enzyme powder or spraydrying the mixture of the aqueous solution of enzyme and a water soluble starch to obtain the enzyme powder.

The β-galactosidase has the optimum pH of 6 to 7 and the optimum temperature of 40° to 50° C in the activation and is stable at lower than 40° C in a pH of 6 to 8.

The enzyme activity of β-galactosidase is determined by incubating it with a substrate of o-nitro-phenyl-β-galactopyranoside (ONPG) at 30° C as 1 ONPG unit for the activity hydrolyzing 1μ mole of ONPG for 1 minute, in accordance with the standard of International Enzyme Committee.

In accordance with the present invention, β-galactosidase is orally administrated to young pig or calf in the lacteal or weaning period to prevent the diarrhea.

It is also effective to administrate β-galactosidase just after suffering the diarrhea, however it is preferable to administrate β-galactosidase before suffering the diarrhea for the preventive effect.

In order to prevent the diarrhea of calf, the dosage of β-galactosidase is usually in a range of 1,000 to 500,000 preferably 10,000 to 60,000 especially 15,000 to 40,000 ONPG units per day.

In order to prevent the diarrhea of young pig, the dosage of β-galactosidase is usually 500 to 100,000 preferably 2,500 to 15,000 especially about 10,000 ONPG units per day.

The optimum administration of β-galactosidase is carried out by adding it to an artifical milk or a feed for calf and to a glucose solution or a feed for young pig.

The β-galactosidase is orally adminstrated by incorporating it in an artifical milk or a feed for weaning.

The following is typical example of the artifical milk for calf before and in the weaning period.

Crude protein: more than 26%
Crude fats and oil: more than 5%
Crude fiber: less than 2%
Crude ash: less than 8%

Sources and Additives

Soybean meal, Fish soluble, Defatted milk powder, Starch, Fat and oil, Whey, Casein, Polysaccharides, Salt, Calcium lactate, Vitamins, Minerals, etc.

Typical artificial milk powder has the following components:

Crude protein: 33.8%
Crude fat and oil: 9.5%
Crude fiber: 0.2%
Crude ash: 8.0%
Water: 12.2%
Digestible crude protein: 27%
Total digestible nutrients: 62%.

The standard amount per day for calf in each age are as follows.

| Age (days) | 5-9 | 10-14 | 15-21 | 22-28 | 29-35 | 36-42 | 43-49 |
|---|---|---|---|---|---|---|---|
| Amount (g/day)** | 200 to 400 | 400 | 600 | 600 | 600 | 600 | 400 |

*The artificial milk is fed for two times in morning and evening
**The artificial milk is diluted with 6 to 10 times of water (about 50° C).

The following is typical example of the feed for calf before or in the weaning period.
 Crude protein: more than 20%
 Crude fat and oil: more than 2.0%
 Crude fiber: less than 5.5%
 Crude ash: less than 8.0%
Sources and Additives
 Corns, brans, Corn meals, Polysaccharides, Alfalfa meal, Vitamins, Minerals, etc..

Typical feed for calf before and in the weaning period has the following components.
 Crude protein: 21.0%
 Crude fat and oil: 4.0%
 Crude fiber: 4.0%
 Crude ash: 7.0%
 Calcium carbonate: 1.5%
 Calcium phosphate: 0.5%
 Digestible crude protein: 18%
 Total digestible nutrient: 73%

The standard amount per day for calf in each age are as follows.

| Age (days) | 10-14 | 15-21 | 22-28 | 29-35 | 36-42 | 43-49 | 50-57 | 58-63 | 64-70 |
|---|---|---|---|---|---|---|---|---|---|
| Amount (g/day) | 100 | 300 | 500 | 800 | 1,200 | 1,600 | 1,800 | 2,000 | 2,100 |

Typical feed for young pig has the following components:

| | | |
|---|---|---|
| Crude protein | 22.2% | 23.0% |
| Crude fat and oil | 5.2% | 5.4% |
| Crude fiber | 0.9% | 0.8% |
| Crude ash | 6.8% | 6.5% |
| Total digestible nutrients | | 86.5% |

The standard amount per day for young pig in each age is as follows:

| Age (day) | 0-10 | 10-15 | 15-20 | 20-25 | 25-30 | 30-35 | 35-40 |
|---|---|---|---|---|---|---|---|
| Amount (g/day) | 50-80 | 80-120 | 100-150 | 150-250 | 200-300 | 300-400 | 400-500 |

* Continuous feeding

In the following experiments, $\beta$-galactosidase enzyme powder is admixed with dextrin to prepare a powdery $\beta$-galactosidase composition having 5000 ONPG units per 1 g.

In the preparation of the powdery $\beta$-galactosidase composition, it is possible to use various powdery carriers which are physically acceptable for young pig and calf such as soluble starch, saccharose, etc.

EXPERIMENT 1

Therapy of diarrhea for sucking pigs

The young pigs were born of Land Race Species (four mother pigs) and four groups of the same mothers were used in the test.

When one of young pigs in one group suffered from the diarrhea, the $\beta$-galactosidase composition was daily administrated at a dosage of 0.5 g (2500 ONPG unit) per day, by a foricible oral administration. The administration was continued until finding the therapeutic result for the diarrhea which was examined by an observation of no diarrheal nor solid feces of bean size.

In accordance with the conventional method, 0.5 ml of Imoposyl (a growth inhibition preventive agent manufactured by Taito-Pfizer Co., Ltd.) and 0.5 ml of Alinimin for animals (Vitamin $B_1$ etc. manufactured by Takeda Yakuhin Kogyo K.K.) were injected to all pigs at 5 to 7 day age.

The number of young pigs in the diarrhea and the observation of feces after the diarrhea and the administration of the $\beta$-galactosidase composition are shown in Table 1 wherein each numerator shows the number of young pigs in the diarrhoea and each denominator shows the number of young pigs in one group.

In Group 1, twelve pigs were born and all pigs were tested. In 12 day age, seven pigs excreted the diarrheal feces in yellow muddy condition. The $\beta$-galactosidase was administrated to all pigs. The excretions were yellow soft feces in the 2nd day, and the excretion for four pigs were the soft feces in the 3rd day and the normal Table 1

| Observation of feces after diarrhea | Group 1 | Group 2 | Group 3 | Group 4 |
|---|---|---|---|---|
| Age suffered in diarrhoea | 12 days | 5 days | 4 days | 3 days |
| 1st day | 7/12 C | 7/7 C | 7/7 D' | 8/8 D |
| 2nd day | 7/12 B | 3/7 C | 7/7 C' | 8/8 C' |
| 3rd day | 4/12 B | 3/7 B' | 7/7 D | 8/8 D' |
| 4th day | 0/12 A | 0/7 A | 7/7 D | 8/8 D |
| 5th day | 0/12 A | 0/7 A | 7/7 C | 8/8 B |
| 6th day | 0/12 A | 0/7 A | 7/7 B | 0/8 A |
| 7th day | 0/12 A | 0/7 A | 0/7 A | 0/8 A |
| Administration | 3 days | 3 days | 6 days | 5 days |

D' yellowish white slurry feces
D yellow slurry feces
C' yellow slurry-muddy feces
C yellow muddy feces
B' yellow muddy-soft feces
B yellow soft feces
A normal feces feces were found for all pigs in the 4th day. The administration was finished.

In Group 2, seven pigs were born and all pigs were tested. In 5 day age, all pigs excreted yellow muddy feces. The $\beta$-galactosidase was administrated. Three pigs excreted the diarrheal feces in the 2nd day and the 3rd day but the normal feces were found for all pigs in the 4th day. The administration was finished.

In Group 3, eight pigs were born and one died due to crushing one day later and seven pigs were tested. In 4 day age, all pigs excreted the series diarrheal feces in yellow slurry condition. The β-galactosidase was administered to all pigs. The excretions were yellow muddy feces in the 2nd day, but were yellow slurry in the 3rd day and 4th day, and were changed to yellow muddy feces in the 5th day and to soft feces in the 6th day. The normal feces were found for all pigs in 7th day. The administration was finished.

In Group 4, nine pigs were born and one died due to crushing one day later and eight pigs were tested.

In 3 day age, all pigs excreted the serious diarrheal feces in yellow slurry condition. The β-galactosidase was administered to all pigs. The excretions were changed to soft feces in the 2nd day but turned to slurry feces in the 3rd day and the 4th day, and changed to soft feces in 5th day. The normal feces were found for all pigs in the 6th day. The administration was finished.

The days for the administration of β-galactosidase and the number of pigs cured are shown in Table 2.

Table 2

| Days for administration of β-galactosidase | number of pigs | percent |
|---|---|---|
| number of pigs in diarrhea | 29 | 85.3% |
| Total pigs | 34 | |
| 1st day | 4 | 13.8% |
| 2nd day | 3 | 10.3% |
| 3rd day | 7 | 24.1% |
| 4th day | 0 | 0 |
| 5th day | 8 | 27.6% |
| 6th day | 7 | 24.1% |
| 7th day | 0 | 0 |

The average weights of pigs in the groups and the weight gains up to 21 day age were shown in Table 3.

Table 3

| Group | Average weight (kg) | | | | Weight gain from born to 21 day age |
|---|---|---|---|---|---|
| | Born | 7 day age | 14 day age | 21 day age | |
| 1 | 1.9 | 2.6 | 3.7 | 4.7 | 2.8 kg |
| 2 | 1.7 | 2.7 | 3.7 | 4.8 | 3.1 kg |
| 3 | 1.5 | 2.1 | 3.4 | 4.1 | 2.6 kg |
| 4 | 1.7 | 3.0 | 4.1 | 5.5 | 3.8 kg |

The weight gain in Group 3 suffered from serious diarrhea was slightly inferior to those of the other Groups, however as a whole, the growth conditions were excellent. The diarrhea was considered to be caused by the secondary infection of colibacilli and those of Groups 3 and 4 were serious diarrhea in Table 3.

It was confirmed that the slight degree of the diarrhea could be cured by the administration of β-galactosidase for 2 to 3 days and the serious degree of the diarrhea could be cured by the administration of β-galactosidase for 5 to 6 days.

In accordance with the administration of β-galactosidase, any side-effect found in the administration of antibiotics was not found and the decrease of weight gain was not found. Accordingly, β-galactosidase was confirmed to be effective.

EXPERIMENT 2

Therapy of diarrhea for 21 young pigs before or in weaning period born of five Land Race Species and three Hampshire Species The β-galactosidase composition was administered once per day at a dosage of 1.0 g (5000 ONPG units) per day by a forcible oral administration without any other therapeutic treatment.

The times of the administrations of β-galactosidase for 21 young pigs until the diarrhea is cured were 5 times in maximum and 1 time in minimum and 1.9 times in average. The results are shown in Table 4.

Table 4

| Object pigs | Times of administrations of β-galactosidase until diarrhea is cured  times | | | | | |
|---|---|---|---|---|---|---|
| | 1 | 2 | 3 | 4 | 5 | no effect |
| 21 | 7 | 11 | 2 | 0 | 1 | 0 |
| | 33.3% | 52.4% | 9.5% | 0% | 4.8% | 0% |

As it is clear from the results, the diarrhea was cured by 1 to 3 times of the administrations of β-galactosidase for 95.2% of young pigs, and non-effective case was not found. The conditions of feces excreted by young pigs were shown in Table 5.

The diarrhea was considered to be caused by the secondary infection of colibacilli from the viewpoints of the day ages and the clinical conditions.

All of young pigs suffered from the diarrhea were cured by the administration of β-galactosidase without any dehydration nor other side-effect. No growth inhibition was found. The fact shows that the administration of the β-galactosidase composition at a dosage of 1.0 g (5000 ONPG units) per day/pig is remarkably effective against the infection of colibacilli.

Table 5

| No. | Young pig Species | Sex | Day age initiating diarrhea | Condition of feces in days after initiation of diarrhoea | | | | |
|---|---|---|---|---|---|---|---|---|
| | | | | 1st | 2nd | 3rd | 4th | 5th |
| 1 | L | ♀ | 14 | ++yw | ++y | — | | |
| 2 | L | ♀ | 15 | ++y | | ++y | +++yg | ++y |
| 3 | L | ♀ | 15 | ++y | — | | | |
| 4 | L | ♀ | 17 | ++yw | +yw | | | |
| 5 | L | ♂ | 19 | ++yw | | | | |
| 6 | H | ♂ | 13 | +++yw | +yg | — | | |
| 7 | L | ♀ | 22 | ++y | +y | — | | |
| 8 | L | ♀ | 25 | +++yg | | | | |
| 9 | L | ♂ | 16 | ++y | | +y | — | |
| 10 | L | ♀ | 16 | ++y | | +y | — | |
| 11 | L | ♂ | 16 | ++y | | +y | | |
| 12 | L | ♀ | 18 | +++yw | — | | | |
| 13 | L | ♂ | 17 | +++yg | +yg | — | | |
| 14 | L | ♂ | 17 | +++yg | +y | — | | |
| 15 | L | ♂ | 17 | +++yg | +y | — | | |
| 16 | L | ♀ | 17 | +++yg | −y | — | | |
| 17 | L | ♂ | 18 | ++y | — | | | |
| 18 | H | ♀ | 23 | ++yw | — | | | |
| 19 | H | ♂ | 23 | ++yw | — | | | |

Table 5-continued

| No. | Young pig Species | Sex | Day age initiating diarrhea | Condition of feces | |
|---|---|---|---|---|---|
| 20 | H | ♀ | 12 | ++y | — |
| 21 | L | ♀ | 16 | ++yw | — |

| | Young pig | | Day age initiating | Condition of feces in days after initiation of diarrhoea | | | | |
|---|---|---|---|---|---|---|---|---|
| No. | Species | Sex | diarrhea | 6th | 7th | 8th | 9th | 10th |
| 1 | L | ♀ | 14 | | | | | |
| 2 | L | ♀ | 15 | | | | | ++yw |
| 3 | L | ♀ | 15 | | | | | |
| 4 | L | ♀ | 17 | | | ++yw | — | |
| 5 | L | ♂ | 19 | ++yw | — | | | |
| 6 | H | ♂ | 13 | | | | | |
| 7 | L | ♀ | 22 | | | | | |
| 8 | L | ♀ | 25 | | | ++y | +y | — |
| 9 | L | ♂ | 16 | | | | | |
| 10 | L | ♀ | 16 | | | | | |
| 11 | L | ♂ | 16 | | | | | |
| 12 | L | ♀ | 18 | | | | | |
| 13 | L | ♂ | 17 | | | | | |
| 14 | L | ♂ | 17 | | | | | |
| 15 | L | ♂ | 17 | | | | | |
| 16 | L | ♀ | 17 | | | | | |
| 17 | L | ♂ | 18 | | | | | |
| 18 | H | ♀ | 23 | | | | | |
| 19 | H | ♂ | 23 | | | | | |
| 20 | H | ♀ | 12 | | | | | |
| 21 | L | ♀ | 16 | | | | | |

| | Young pig | | Day age initiating | Condition of feces in days after initiation of diarrhoea | | Days for |
|---|---|---|---|---|---|---|
| No. | Species | Sex | diarrhea | 11th | 12th | administration |
| 1 | L | ♀ | 14 | | | 2 |
| 2 | L | ♀ | 15 | — | | 5 |
| 3 | L | ♀ | 15 | | | 1 |
| 4 | L | ♀ | 17 | | | 3 |
| 5 | L | ♂ | 19 | | | 2 |
| 6 | H | ♂ | 13 | | | 2 |
| 7 | L | ♀ | 22 | | | 2 |
| 8 | L | ♀ | 25 | | | 3 |
| 9 | L | ♂ | 16 | | | 2 |
| 10 | L | ♀ | 16 | | | 2 |
| 11 | L | ♂ | 16 | | | 2 |
| 12 | L | ♀ | 18 | | | 1 |
| 13 | L | ♂ | 17 | | | 2 |
| 14 | L | ♂ | 17 | | | 2 |
| 15 | L | ♂ | 17 | | | 2 |
| 16 | L | ♀ | 17 | | | 2 |
| 17 | L | ♂ | 18 | | | 1 |
| 18 | H | ♀ | 23 | | | 1 |
| 19 | H | ♂ | 23 | | | 1 |
| 20 | H | ♀ | 12 | | | 1 |
| 21 | L | ♀ | 16 | | | 1 |

Notes:
Conditions of feces
— : normal condition
± : slightly soft feces
+ : soft feces
++ : muddy feces
+++ : slurry feces
Colors :
yellow: y
yellowish white: yw
yellowish green: yg
The β-galactosidase was administrated in the cases of ± to +++.

EXPERIMENT 3

Therapy of diarrhea for young pigs before or in weaning period by administration of water containing β-galactosidase Eighteen young pigs born of Land Race Species in two groups were tested. When the diarrhea was found for certain young pigs in each group, β-galactosidase was dissolved in water for drink and the aqueous solution was administrated as a free drinking water. The amount of β-galactosidase composition was at a dosage of 1.0 g (5000 ONPG units) per day per pig, and it was dissolved in water drunk for 1 day and the drinking water was fed through automatic water feeders for young pigs, without any other therapeutic treatment.

The conditions of feces excreted by pigs in the diarrhea in each group are shown in Table 6. The references in Table 6 are the same with those of Table 5.

Table 6

| Group | Species | Day age suffered in diarrhoea | Pig in diarrhoea No. | Sex | Conditions of feces after diarrhoea (days) 1st | 2nd | 3rd | 4th | Days for administration |
|---|---|---|---|---|---|---|---|---|---|
| | | | 1 | ♂ | +++yw | ++y | +y | — | |
| | | | 2 | ♀ | +++yw | ++y | +y | — | |

Table 6-continued

| Group | Species | Day age suffered in diarrhoea | Pig in diarrhoea No. | Sex | Conditions of feces after diarrhoea (days) 1st | 2nd | 3rd | 4th | Days for administration |
|---|---|---|---|---|---|---|---|---|---|
| 1. | L | 8 (8 pigs) | 3 | ♂ | — | +++ y | + y | — | 3 |
|  |  |  | 4 | ♀ | — | +++ yw | + y | — |  |
|  |  |  | 1 | ♀ | ++ yw | ++ y | + y | — |  |
|  |  |  | 2 | ♀ | ++ yw | ++ y | + y | — |  |
|  |  |  | 3 | ♂ | ++ yw | ++ y | + y | — |  |
| 2 | L | 28 (10 pigs) | 4 | ♀ | ++ yw | ++ y | + y | — |  |
|  |  |  | 5 | ♂ | +++ yw | ++ y | + y | — |  |
|  |  |  | 6 | ♂ | ++ yw | ++ y | + y | — |  |

In Group 1, in 8 day age, two of eight pigs excreted the diarrheal feces in yellowish white slurry condition. The β-galactosidase was administrated to all pigs. The excretions of the two pigs were changed to yellow muddy feces but other two pigs excreted the diarrheal feces in the 2nd day. The excretions of the four pigs were changed to soft feces in the 3rd day and to the normal feces in the 4th day. The administration was finished.

In Group 2, of 28 day age, six of ten pigs excreted the diarrheal feces in yellowish white slurry to muddy conditions. The β-galactosidase was administrated. The excretions were changed to yellow soft feces in the 3rd day and to the normal feces in the 4th day.

The diarrhea in Groups 1 and 2 was considered to be caused by the secondary infection of colibacilli from the viewpoints of the conditions of feces and the clinical conditions. All of young pigs suffered from the diarrhea were cured by the administration of β-galactosidase for 3 days without any disadvantageous effect.

The fact shows that the administration of β-galactosidase in the drinking water is effective.

EXPERIMENT 4

All of pigs born of each of four mothers were grouped into each of two subgroups.

In each of subgroups, the β-galactosidase composition was administrated once per day at a dosage of 0.25 to 0.5 g (1250 to 2500 ONPG units) per day by a forcible oral administration from the born to the weaning period.

In the other subgroups, the β-galactosidase was not administrated.

The results are shown in Table 7.

Table 7

| Group | Subgroup | Average weight in born (kg) | Average weight gain from born to weaning | Day age in weaning |
|---|---|---|---|---|
| 1 | 0.25 g of the composition | 1.50 (3)* | 0.249 (116.9)** | 26 day age |
|  | control | 1.53 (3) | 0.213 |  |
| 2 | 0.25 g of the composition | 1.13 (4) | 0.198 (109.4) | 25 day age |
|  | control | 1.18 (4) | 0.181 |  |
| 3 | 0.5 g of the composition | 1.36 (5) | 0.177 (114.9) | 28 day age |
|  | control | 1.28 (5) | 0.154 |  |
| 4 | 0.5 g of the composition | 1.80 (4) | 0.206 (109.6) | 28 day age |
|  | control | 1.58 (4) | 0.188 |  |

Note: 0.25 g of the composition: Administration of 0.25 g (2500 ONPG units) of β-galactosidase composition.
*number of pigs
**Rate of average weight gain per 100 of control.

In the controls, the diarrhea was found for 20 to 50% of pigs whereas in the subgroups for the administration of β-galactosidase, the diarrhea was found only for one pig (0.25 g subgroup) for one time.

In the controls, the excretions of soft feces were found before or in the weaning period, whereas in the subgroups for the administration of β-galactosidase, the excretions were normal. It was confirmed that the diarrhea was prevented before and in the weaning period.

In Table 7, the average weights in born and the average weight gain from the born to the weaning are shown. It was found that the weight gains for the subgroups of the administration of β-galactosidase are higher than those of the control, for about 10 to 17%.

As the results, it was found that the continuous administration of β-galactosidase prevents the diarrhea of young pig and is effective for the growth promotion in sucking period to give high productivity.

EXPERIMENT 5

Therapy of diarrhea for calf in sucking period

The effect of β-galactosidase was tested by using seven calves in the sucking period from 10 day age to 90 day age which suffered in the diarrhea. The β-galactosidase composition was admixed with the artificial milk at a ratio of 1.0 g (5000 ONPG units) per 60 to 80 g of the artificial milk. The milk was continuously fed in each lactation until the therapeutic result to the diarrhea was found. The results are shown in Table 8.

Table 8

| No. | Day age introduced | Day age initiating diarrhea | Day age initiation of administration | Terms for administration (day) | Total dosage (g) | Dosage per day (g) |
|---|---|---|---|---|---|---|
| 1 | 20 | 42 relapsed 63 | 49 63 | 10 10 | 65 70 | 6.5 7.0 |
| 2 | 14 | 22 | 29 | 14 | 72 | 5.1 |
| 3 | 20 | 50 | 50 | 2 | 12 | 6.0 |
| 4 | 17 | 44 | 44 | 7 | 42 | 6.0 |
| 5 | 13 | 24 | 25 | 5 | 30 | 6.0 |
| 6 | 15 | 23 | 23 | 4 | 24 | 6.0 |
| 7 | 14 | 18 | 18 | 6 | 37 | 6.2 |

| Typical clinical conditions and notes |
|---|
| No. 1: The diarrhea was found after catching cold. Once the diarrhea was cured but was relapsed because of cold. The diarrhea was cured after the cure of cold. Once the cure was found but the diarrhea was relapsed. Ineffective |
| No. 2: Yellow diarrheal faces → Grayish white slurry feces → die in pneumonia Ineffective: |
| No. 3: Brown diarrheal feces → Cured: |
| No. 4: Yellow diarrheal feces → Catching cold → Reconvalescence by administration for 3 days → Cured: |
| No. 5: Grayish white diarrheal feces → Reconvalescence by administration for 2 days → |

|   | Typical clinical conditions and notes |
|---|---|
| No. 6: | Cured:<br>Yellow diarrheal feces →<br>Cured: |
| No. 7: | Grayish white slurry feces<br>depressed → Cured: |

Five of seven calves were cured. The percentage of cure including the temporary cure was 85.7%. In the two ineffective cases, the administration of β-galactosidase was initiated 7 days after the diarrhea and they suffered in the other diseases to be bad diarrheal condition.

In the other cases administrating β-galactosidase from the initiation of the diarrhea, the cures were found for 2 to 7 days in an average of 4.8 days under an average dosage of 6 g of the β-galactosidase composition per day.

The diarrhea was considered to be caused by the secondary infection of colibacilli from the viewpoint of clinical condition. During the therapeutic period, the dehydration and the other side effect were not found and the weight loss of the calves was not found. After the cure, the growths of the calves were in the normal condition. As the results, it was confirmed that the administration of β-galactosidase in the artificial milk for the calves suffered in the diarrhea is quite effective at the initiation of the diarrhea.

In the case of calves, the other diseases such as pneumonia are easily caused. Accordingly, it is further effective to administrate β-galactosidase together with the other antibiotic.

As it is clear from the experiments, β-galactosidase is remarkably effective for preventing the diarrhea of young pig and calf in the sucking period to the weaning period. The dehydration and the other side-effect caused by the administration of antibiotics do not find in the administration of β-galactosidase. The resistance to β-galactosidase is not found and accordingly, the resistive microorganism is not formed. The administration of β-galactosidase can be easily carried out by an addition in a drinking water, a feed, an artificial milk, etc. without limiting to the forcible oral administration.

Moreover, β-galactosidase can be administrated together with the administration of an antibiotic etc., if necessary.

What is claimed is:

1. A method of preventing diarrhea in suckling or weaning pigs or calves which comprises orally administering an effective amount of β-galactosidase to said pigs or calves during at least a portion of the lacteal or weaning periods.

2. The method of claim 1, wherein said β-galactosidase is orally administered in the form of a milk solution or a drinking water solution to said pigs or calves in said lacteal period.

3. The method of claim 1, wherein said β-galactosidase is orally adminisered in the form of a feed mixture to said pigs or calves in said weaning period.

4. The method of claim 1, wherein said effective amount for pigs is from 500 to 100,000 ONPG units per day.

5. The method of claim 1, wherein said effective amount for calves is from 1,000 to 500,000 ONPG units per day.

6. A method of preventing diarrhea in suckling or weaning pigs or calves which comprises orally administering an effective amount of β-galactosidase to said pigs or calves during at least a portion of the lacteal or weaning periods, and wherein said β-galactosidase is stable in the stomach of said pigs or calves.

7. A method of preventing diarrhea in suckling or weaning pigs or calves which comprises orally administering an effective amount of β-galactosidase derived from Kluyveromyces lactis to said pigs or calves during at least a portion of the lacteal or weaning periods.

* * * * *